US009836178B2

(12) United States Patent
Twig et al.

(10) Patent No.: US 9,836,178 B2
(45) Date of Patent: Dec. 5, 2017

(54) SOCIAL WEB BROWSING

(71) Applicant: Yahoo! Inc., Sunnyvale, CA (US)

(72) Inventors: Ilan Twig, Campbell, CA (US); Eyal Ophir, Palo Alto, CA (US)

(73) Assignee: EXCALIBUR IP, LLC, New York, NY (US)

( * ) Notice: Subject to any disclaimer, the term of this patent is extended or adjusted under 35 U.S.C. 154(b) by 156 days.

(21) Appl. No.: 13/668,249

(22) Filed: Nov. 3, 2012

(65) Prior Publication Data

US 2013/0117675 A1 May 9, 2013

Related U.S. Application Data

(60) Provisional application No. 61/555,475, filed on Nov. 3, 2011.

(51) Int. Cl.
*G06F 3/048* (2013.01)
*G06F 17/30* (2006.01)
(Continued)

(52) U.S. Cl.
CPC ........ *G06F 3/048* (2013.01); *G06F 17/30867* (2013.01); *G06F 3/0482* (2013.01);
(Continued)

(58) Field of Classification Search
CPC .. G06F 3/0481; G06F 3/0482; G06F 19/3406; G06F 3/04817; G06F 3/0485;
(Continued)

(56) References Cited

U.S. PATENT DOCUMENTS 8,489,515 B2 * 7/2013 Mathur .................. 705/319
8,626,823 B2 * 1/2014 Kumar .................. 709/203
(Continued)

OTHER PUBLICATIONS

PCT International Search Report and Written Opinion, PCT Application No. PCT/US12/63465, dated Jan. 18, 2013, 14 pages.

*Primary Examiner* — Abdullah Al Kawsar
*Assistant Examiner* — Jian Yu
(74) *Attorney, Agent, or Firm* — Weaver Austin Villeneuve & Sampson LLP

(57) ABSTRACT

A method of guiding a user's web navigation through the recommendation of online content in the form of a navigation recommendation includes a server and a browser. The browser receives identification associated with a user in a navigation network and transmits the login information to the server. The browser additionally transmits information about the user's browsing activity to the server. The server receives browsing activities from many browsers having associated users and stores information indicating an association between the users and their respective interactions. The server additionally receives social networking information for the users and stores information indicating an association between the user and their respective social connections. Based on an input received from the browser associated with the user in the navigation network, the server determines a navigation recommendation for the user based on the stored information and transmits the navigation recommendation to the browser.

26 Claims, 9 Drawing Sheets

(51) Int. Cl.
   *G06F 3/0482* (2013.01)
   *G06F 19/00* (2011.01)
   *G06F 3/0481* (2013.01)
   *G06F 3/0485* (2013.01)

(52) U.S. Cl.
   CPC ........ *G06F 3/0485* (2013.01); *G06F 3/04817* (2013.01); *G06F 19/322* (2013.01); *G06F 19/3406* (2013.01)

(58) Field of Classification Search
   CPC .. G06F 19/322; G06F 3/048; G06F 17/30867; H04L 41/22; H04L 41/12
   USPC .......................................................... 715/737
   See application file for complete search history.

(56) References Cited

U.S. PATENT DOCUMENTS

| | | | | |
|---|---|---|---|---|
| 2005/0033803 A1* | 2/2005 | Vleet | ................ | G06F 17/30867 709/203 |
| 2006/0248078 A1* | 11/2006 | Gross | ................ | G06F 17/3064 |
| 2007/0067305 A1* | 3/2007 | Ives | ................ | 707/10 |
| 2007/0260520 A1 | 11/2007 | Jha et al. | | |
| 2008/0209343 A1* | 8/2008 | Macadaan et al. | ........... | 715/747 |
| 2009/0006195 A1* | 1/2009 | Rosen | .................... | G06Q 30/02 705/14.1 |
| 2009/0006388 A1 | 1/2009 | Ives et al. | | |
| 2009/0083232 A1* | 3/2009 | Ives et al. | ......................... | 707/3 |
| 2010/0057675 A1* | 3/2010 | White | .................... | G06Q 30/02 707/E17.108 |
| 2010/0082593 A1 | 4/2010 | Singh | | |
| 2010/0179964 A1* | 7/2010 | Ramaswamy | ...... | G06F 17/3064 707/780 |
| 2012/0011432 A1* | 1/2012 | Strutton | ........................ | 715/234 |
| 2012/0131032 A1* | 5/2012 | Rakshit | ............. | G06F 17/30873 707/767 |
| 2012/0136941 A1* | 5/2012 | Howes | .................... | H04L 51/14 709/206 |
| 2012/0197927 A1* | 8/2012 | Qian | ................. | G06F 17/30702 707/769 |
| 2012/0215846 A1* | 8/2012 | Howes | .................... | G06Q 10/10 709/204 |
| 2012/0260157 A1* | 10/2012 | Zhu | .................... | G06F 17/30902 715/234 |
| 2013/0159271 A1* | 6/2013 | Ophir | .................... | G06F 17/30867 707/706 |

* cited by examiner

SOCIAL WEB BROWSING

CROSS REFERENCE TO RELATED APPLICATIONS

This application claims the benefit of U.S. Provisional Application No. 61/555,475, filed on Nov. 3, 2011, which is incorporated by reference herein in its entirety.

BACKGROUND

1. Field of Art

The present invention generally relates to the field of web browsing and more specifically to recommending content to those browsing the web.

2. Background Information

Users interact with webpages and other types of content online using a wide range of computing devices. Oftentimes, the users desire to know what content other users are interacting with so they too can experience it. There are a number of advantages to knowing about and experiencing similar content, such as being aware of others interests, generating discussion, and trying new things.

However, a user is often unaware of content other users interact with unless the content is shared directly with the user. Additionally, even if a given user chooses to share content, other users may not find the content relevant to their current activities or interests and ignore it. Other factors further inhibit users from discovering content as it relates to their current activities or interests, such as when and where it is provided or shared. Furthermore, many users choose not to share content they find interesting. These difficulties prohibit users from experiencing content when it relates to their current activities and interests.

SUMMARY

Embodiments of the invention enable a browser, such as a web browser at client, to guide a user's web navigation through the recommendation of online content in the form of a navigation recommendation displayed for the user as it relates to their activities at the browser.

A method of guiding a user's web navigation includes a browser and a navigation server. The browser receives identification associated with a user in a navigation network maintained by the navigation server. The browser additionally collects information, such as the user's browsing activity, indicating the user's interactions with information it displays. The user's browsing activity is transmitted to the navigation server which stores the browsing activity in the navigation network in association with the user. The navigation server additionally receives browsing activities associated with other users. Interests of the users are determined based on their respective browsing activities and stored in the navigation network. In addition to receiving browsing activities, the navigation server receives social graphs corresponding to various users' social networking accounts. The navigation server associates users in the navigation network with their respective social networking connections based on the social graphs. In this manner, the navigation server forms relationships in the navigation network between users, their interests and online content. The navigation server uses the navigation network to recommend content to the user and indicate, to the user, why the content is being recommended. When the navigation server receives input indicating data on the internet, such as a content item, keyword, feed, etc., from a browser associated with the user, the navigation server determines a navigation recommendation based on the input and the information stored in the navigation network. The navigation recommendation includes recommended content and associated information for respective content recommendations describing the user's association with the recommended content and thus the reason for the recommendation. The navigation server transmits the navigation recommendation to the browser which subsequently displays the navigation recommendation to the user. Accordingly, the method beneficially allows the user to navigate online content as it relates to their input, interests and social network.

The features and advantages described in the specification are not all inclusive and, in particular, many additional features and advantages will be apparent to one of ordinary skill in the art in view of the drawings, specification, and claims. Moreover, it should be noted that the language used in the specification has been principally selected for readability and instructional purposes, and may not have been selected to delineate or circumscribe the disclosed subject matter.

DETAILED DESCRIPTION

The computing environment described herein enables guiding website navigation. The Figures (FIGS.) and the following description describe certain embodiments by way of illustration only. One skilled in the art will readily recognize from the following description that alternative embodiments of the structures and methods illustrated herein may be employed without departing from the principles described herein. Reference will now be made to several embodiments, examples of which are illustrated in the accompanying figures. It is noted that wherever practicable similar or like reference numbers may be used in the figures and may indicate similar or like functionality.

System Environment

Figure 1:
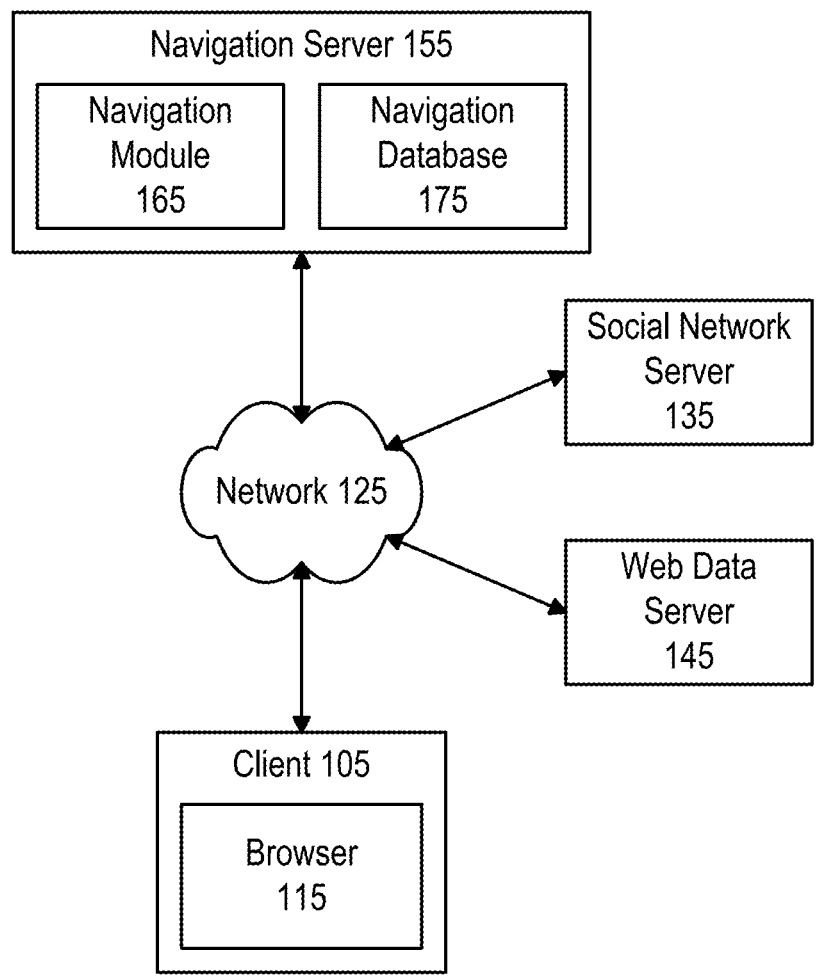
FIG. 1 is a block diagram illustrating an environment for guiding website navigation according to one embodiment.

Referring to FIG. 1, the computing environment 100 for guiding website navigation at a client 105 includes a network 125, an external social network server 135, a web data server 145 and a navigation server 155. While only one client 105 and one server 155 are shown in FIG. 1 for clarity, embodiments can have many clients 105 and multiple instances of the servers 135, 145, 155.

The client 105 is a computing system with a processor and memory capable of running applications, such as a browser 115 that users interact with to view content on the network 125 and for guiding navigation of the content. Examples of the client 105 include a desktop, notebook, or tablet computer, a mobile telephone, or television set-top box.

The browser 115 is an application for retrieving data from and sending data to various entities on the network 125, presenting data on a display of the client 105 and authenticating users. The browser 115 also transmits navigation requests to and receives corresponding navigation recommendations from the navigation server 155. For example, the browser 115 authenticates a user, receives input from the authenticated user, determines information about the input for a navigation request, and transmits the navigation request to the navigation server. The information about the input can include the input and a Uniform Resource Locator "URL," keyword or category associated with the input. The browser 115 subsequently receives a navigation recommendation corresponding to the request and presents information therein to the user. Embodiments of the browser 115 store users' browsing activity and transmit the browsing activity to the navigation server 155. The transmitted browsing activity information is then used by the navigation server 155 to make navigation recommendations for users. Additionally, some embodiments of the browser 155 transmit user identification "ID" information with the navigation request to the navigation server 155. The transmitted user ID is used by the navigation server 155 to make navigation recommendations specific to the user. In some embodiments, browser functionality may be incorporated into a media player, video game, widget, set-top box application, etc., to guide website navigation.

The social network server 135 collects and stores data about social networking entities and their interactions with other social networking entities within a social network in social graphs. A social networking entity is the representation of a person, group, place, thing, etc., within the social network. Some example representations of an entity are webpages, profiles, feeds or channels. The social graphs describe the type and number of interactions the entities performed during their social networking activities. Examples of an entity's interactions include tagging, liking, posting, friending, visiting, linking, chatting, or otherwise interacting with another entity as part of the social networking experience. In one embodiment, the social graph of an entity indicates friends of the entity, friends' profiles the entity viewed or tagged, content the entity associated with their profile and content the entity liked or viewed. In some embodiments, social graphs also describe social networking entities' interactions with entities outside the social network, such as online entities including webpages, websites or URLs, by tracking how often an entity posts about, accesses, or otherwise interacts with an online entity on or through the social network.

The web data server 145 collects data and stores data about online entities and users' interactions with them. This stored data, like social graphs, can be used to make navigation recommendations. As used herein, online entities, or web content, includes the body or specific instances of content items such as websites, webpages and media accessible on the network 125 at associated URLs. In one embodiment, the web data server 145 collects, for a given online entity such as a website or browser 115 accessing the website, information like an identifier or URL of the website, a timestamp, an Internet Protocol "IP" address associated with the browser, and the previously or next visited content. In one embodiment, the web data server 145 hosts a URL shortening service and collects data on users accessing web content via the shortened URLs. The web data server 145 ranks and categorizes the accessed web content corresponding to the shortened URLs based on views, co-visits, content, and accessing user demographics. In some embodiments, the web data server 145 hosts a search engine that stores search results/rankings describing browsing trends of users accessing web content over the network 125.

The navigation server 155 is a computing system with a processor and memory that includes a navigation module 165 and a navigation database 175. The navigation database 175 receives and stores data from browsers 115, social network servers 135 and web data servers 145. The navigation module 165 processes received data and determines the navigation recommendations provided to the browser 115. The navigation module 165 is described below with reference to FIG. 3.

In some embodiments, the web data server 145 or navigation server 155 collect and store users' browsing activity, user specified data, inferred data about a user and feeds favorited or associated by a user. Systems and methods for tracking and storing such information are disclosed in U.S. patent application Ser. No. 12/720,394, which is incorporated herein by reference in its entirety.

The network 125 represents the communication pathway between clients 105 and servers 135, 145, 155. In one embodiment, the network 125 uses standard communications technologies or protocols and is the Internet. In other embodiments, the network can also use custom or dedicated data communications technologies instead of, or in addition to, the Internet. The network 125 can also use dedicated or private communications links that are not necessary part of the Internet.

In one embodiment, a user enters authentication information for a browser account at the browser 115. The browser 115 authenticates the browser account with the navigation server 155. Additionally, in one embodiment, the user enters authentication information for their social networking accounts or data services at the browser 115.

The navigation server 155 collects and processes data from browsers 115, social network server 135 or web data server 145 for the user's browser account. The navigation server 155 processes associated browsing activity, social graphs and web data to determine relationships and data for storage in a navigation network for the browser account. The navigation server 155 uses the navigation network to determine browsing recommendations for the user.

The browser 115 then receives user input, for example in the address bar or search bar of the browser, and the browser 115 requests a navigation recommendation. The navigation server 155 receives the request from the browser 115 and, in turn, determines a corresponding navigation recommendation based on the request and information stored in the navigation network for the browser account. In one embodiment, the determined recommendation includes URLs or search terms relevant to the request.

To determine the recommendation, the navigation server 155 maps the request to entities that are relevant to the request. For example, if the request information includes a racing driver's name, the navigation server 155 maps the request to the racing driver's website and additional entities such as websites A, B and C based on relationships stored for the requesting user.

The navigation server 155 determines which websites are relevant to the user by crosschecking websites A, B and C and the driver's website against the browser account's relationships. The crosschecking indicates which websites are related (directly or indirectly) to the user's browsing account. Assume, for example, the browser account is "friends" with user X that "liked" website A and "friends" with user Y that visited website B. The crosschecking indicates that both website A and website B are related to the browser account through shared connections, user X and user Y, respectively. The navigation server 155 provides the websites that are related to the user in the navigation recommendation.

Additionally, the navigation server 155 includes profile images of the shared connections in the navigation recommendation as associated information describing the relevance of website A and website B to the requesting browser account (e.g., via the indication that user X interacted with website A). Other examples of associated information include the number of users that "liked", tagged, or shared website A and visited website B. The navigation server 155 transmits the navigation recommendation to the browser 115 for presentation.

The browser 115 presents the navigation recommendation by displaying the received URLs with profile images of the shared connections and the other associated information.

The description about the client 105, the browser 115, the external social network server 135, the web data server 145 and the navigation server 155 assigns particular functions to one entity or another. This description and the functions assigned are for illustration purposes and to not limit servers or clients to their assigned functions. Upon reading this disclosure, one of ordinary skill in the art will understand that functions described in one embodiment as being performed on the server side can also be performed on the client side in other embodiments if appropriate. Additionally, the functionality attributed to a particular component can be performed by different or multiple components operating together, as deemed appropriate by the implementer.

Browser

Figure 2:
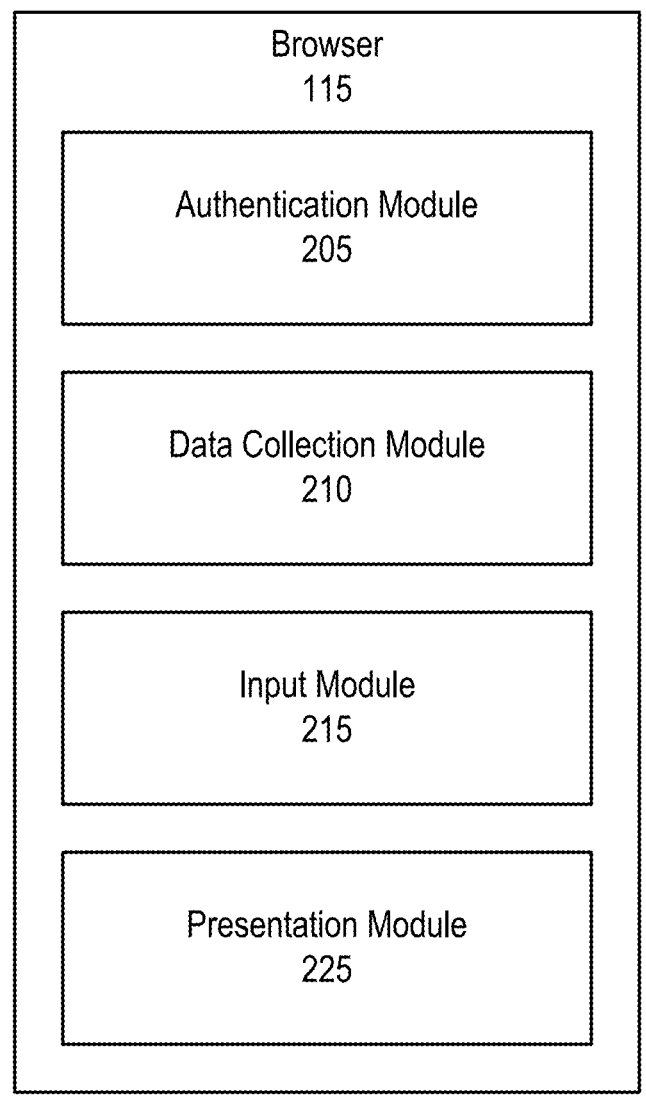
FIG. 2 is a block diagram illustrating a browser for guiding website navigation according to one embodiment.

FIG. 2 is a block diagram illustrating the browser 115 according to one embodiment. The browser 115 includes an authentication module 205, a data collection module 210, an input module 215 and a presentation module 225.

The authentication module 205 receives authentication data from the user and authenticates the user for a given browser account. In one embodiment, the authentication data comprises user ID and a corresponding password. The user ID and password are alpha-numeric string associated with the user. The authentication module 205 transmits the authentication data to navigation server 155 or another authenticating entity (not shown) and receives authentication results for the given browser account.

In one embodiment, the browser account is a social networking account and the authentication data comprises a social networking ID and a corresponding password. The authentication module 205 transmits the authentication data to a corresponding social networking server 135 or the navigation server 155 and receives the results.

In one embodiment, the authentication module 205 also registers new browsing accounts for users. Thus, the authentication module prompts the user for a desired login and password for the new browsing account. The authentication module 205 transmits the desired login and the password for the new browsing account to the navigation server 155 and receives account registration results.

After the authentication module 205 authenticates the user's browsing account, the data collection module 210 starts collecting information associated with the user's interaction with the browser 115. Information on interactions with online entities, such as browsing patterns or browsing activities, collected after authentication of a browser account may be directly associated with the user's browser account. In some embodiments, information collected prior to authentication is also directly or selectively associated with the user's browser account or other browser accounts.

Some embodiments of the authentication module 205 prompt users to associate additional account or data service information with their browser account. For example, the authentication module 205 prompts the user for authentication data for one or more of the user's social networking accounts registered with a given social network server 135. In another example, the authentication module 205 prompts the user for information about one or more of the user's web data services, e.g., a feed subscribed to or plug-in service used by the user and provided or supported by a web data server 145. The authentication module 205 transmits received social network authentication data or web data service subscription information to the navigation server 155.

The input module 215 detects and receives user interactions at the browser 115 or in widgets associated with the browser 115 for data collection by the data collection module 210 and transmission to the navigation server 155 or another entity. In one embodiment, the input module 215 receives inputs such as a user selection (e.g., scroll-overs, clicks, etc.) of displayed content or as user entered data (e.g., text, voice, image data, etc.) at the browser 115. The input module 215 transmits information about the input to the navigation server 155, data collection module 210 or another entity. For example, the input module 215 transmits user entered text and a location where the text was entered to the navigation server 155. In another example, a user selects a selectable navigation element associated with online content such as a URL or image and the input module 215 transmits the URL and information about selectable navigation element to the navigation server 155. Selectable navigation elements are described below in conjunction with the presentation module 225.

In one embodiment, the input module 215 receives input associated with requesting a navigation recommendation and determines a navigation request to transmit to the navigation server 155. For example, the user enters text in an address bar, search bar or selects a navigation element within the browser 115. The input module 215 receives the user input and determines a navigation request. The request includes information about the input such as entered text or selected textual content. In one embodiment, the request also includes associated information describing where the input was received and preferences about content to receive in the navigation request. One example request indicates that textual input was received at an address bar of the browser 115 and includes the entered text. Other requests may alternatively indicate, for example, selection of content within a navigation recommendation, content associated with a navigation element.

Additionally, some embodiments of the input module 215 may determine a navigation request for updating a navigation recommendation feed. Feed updates may be requested in response to the user's selection of an icon representing a specific feed or in the background for one or more feeds. The feeds are associated with a specified website or keyword or service that is indicated in the request. In one example, the input module 215 determines a navigation request including one or more URLs associated with a webpage currently being viewed by the user. In another example, the input module 215 determines a navigation request including one or more URLs or keywords previously specified (e.g., in a favorites or history) or frequented by the user. Other examples include determining a navigation request for top ranked recommendations in the user's navigation network that are displayed in a top ranked feed. User specified options associated with determining requests for navigation recommendation feed updates may be stored at the data collection module 210 or navigation server 155. Examples of user specified options are websites, categories of websites or keywords for which feeds are generated. If user specified options are stored at the navigation server 155, navigation requests may also be determined at the navigation server and corresponding recommendations pushed to the user to automatically update the feeds.

The data collection module 210 receives and stores data for the browser 115. In one embodiment, the data collection module receives data from the input module 215 describing user interactions at the browser 115 and data from the presentation module 220 describing information received or displayed at the browser 115. For example, the data collection module 210 stores browsing activity data associated with accessing various online entities such as, bookmarks, saved searches, website addresses the user inputs in the address bar, search terms the user enters in a search toolbar or a search page, visited website addresses and web content selected within websites. In one embodiment, the data collection module 210 stores the frequency with which the user inputs or visits the same or similar content. In another embodiment, the data collection module 210 tracks and stores the amount of time the user spends on particular web content such as a website, picture or video. The data collection module 210 may also store authentication data for social networking accounts, web data service subscriptions or any other information entered by the user in widgets associated with the browser 115 or content displayed by the browser 115. The data collection module 210 periodically transmits all or part of this stored information to the navigation server 155 for processing and recommendation of content to the user. In some embodiments, user configurable options at the data collection module 210 specify the data to be received from or sent to the navigation server 155 or another entity. For example, users may configure these options to opt out or into sharing certain identifiable information such as their browsing activity with the navigation server 155 over a specified time period or while browsing a specific website or domain of websites.

The presentation module 225 receives data from the navigation server 155 and other entities on the network 125 and presents the received data to the user. For example, the presentation module 225 receives navigation recommendations and presents them on the display 418 of the client 105. In one embodiment, the presentation module 225 presents a received navigation recommendation responsive to a user entering text in the address bar or the search bar of the browser 115. In another embodiment, the presentation module 225 presents a received navigation recommendation responsive to a user selecting a navigation element associated with displayed web content.

In one embodiment, a navigation recommendation includes one or more browsing recommendations and associated information. Examples of browsing recommendations include search terms and URLs. The associated information conveys additional information about the browsing recommendations such as the browsing recommendations' social relevance to the user's browser account. Examples of socially relevant information convey the identity of a shared connection with an image, profile picture or account name of the social networking entity that viewed, interacted with or is otherwise related to the browsing recommendation. Additional examples of socially relevant information convey the number of other users or the user's friends who have recommended or viewed content associated with the URL or search term. Other examples of associated information for a given browsing recommendation include a description or title of the content, an image associated with the content, a popularity or rank of the content as it relates to the user or general body of users, a number of comments, etc. In some embodiments, the navigation recommendations include URLs for the associated information. The presentation module 225 displays one or more browsing recommendations and their associated information at the client 105.

The user interacts with the displayed navigation recommendation to navigate to recommended content. For example, the user selects a browsing recommendation for a URL specifying the location(s) of web content on the network 125. The presentation module 225 subsequently retrieves and displays the web content, e.g., by navigating to the website or webpage specified by the URL.

In one embodiment, the presentation module 225 receives additional browsing recommendations, and optionally the associated information, based on user selections within a currently displayed navigation recommendation. For example, if a user scrolls-over a recommended search term, the presentation module 225 receives and displays additional browsing recommendations and optionally the associated information. Thus, the presentation module 225 allows the user to preview a navigation recommendation (and optionally select information therein) before committing to a selection within the currently displayed navigation recommendation.

In some embodiments, the presentation module 225 analyzes received web content to determine navigation recommendations for various web objects, like links, in the received web content. Thus, for example, the presentation module 225 can associate selectable navigation elements proximate to URLs, images and other selectable web content. In one embodiment, a selectable navigation element is an icon associated with web content that, when selected, causes the browser 115 to display a navigation recommendation.

To associate navigation elements, in one embodiment, the presentation module 225 analyzes HyperText Markup Language "HTML" of web content to determine the selectable content in a webpage. For example, the presentation module 225 determines embedded media and links to other webpages or content and keywords responsive to tags in the HTML and URL information. In another example, the presentation module 225 determines that an embedded URL ending in .avi is for a video file and .jpg is for an image. The presentation module 225 then overlays a selectable navigation element proximate to the determined selectable content. Other embodiments of the presentation module 225 modify the HTML code to display selectable navigational elements proximate to the selectable content. For example, the presentation module 225 inserts HMTL code for displaying the selectable elements at locations in webpage HTML code adjacent to the selectable web content. The presentation module 225 can also modify HTML code to visually change the display of the selectable content to indicate that a navigation request can be generated, e.g., by highlight text or creating a border around an image or video, etc.

In one embodiment, the presentation module 225 analyzes the webpage HTML code to determine unobtrusive navigation element display locations that do not alter the display webpage content. For example, the presentation module 225 determines whitespace or background areas proximate to selectable content and displays navigation elements in the determined areas. In one embodiment, the presentation module 225 creates one or more HTML i-frames and displays the navigation elements responsive to the determined locations as overlays of the webpage in the HTML i-frames.

Additionally, some embodiments of the presentation module 225 receive navigation recommendations for display as feeds. In one embodiment, icons representing various available feeds or user specified feeds are displayed proximate to the viewing area of the browser 115. Options to opt in or out of each feed are presented to the user. Additionally, an option to opt in or out of transmitting the user's browsing activity while navigating content associated with the feed is displayed. In response to the user selection of an icon such as "CNN" for "www.CNN.com," the presentation module 225 displays (e.g., in a window) the received navigation recommendations corresponding to the feed, including the browsing recommendations and the associated information.

Navigation Module

Figure 3:
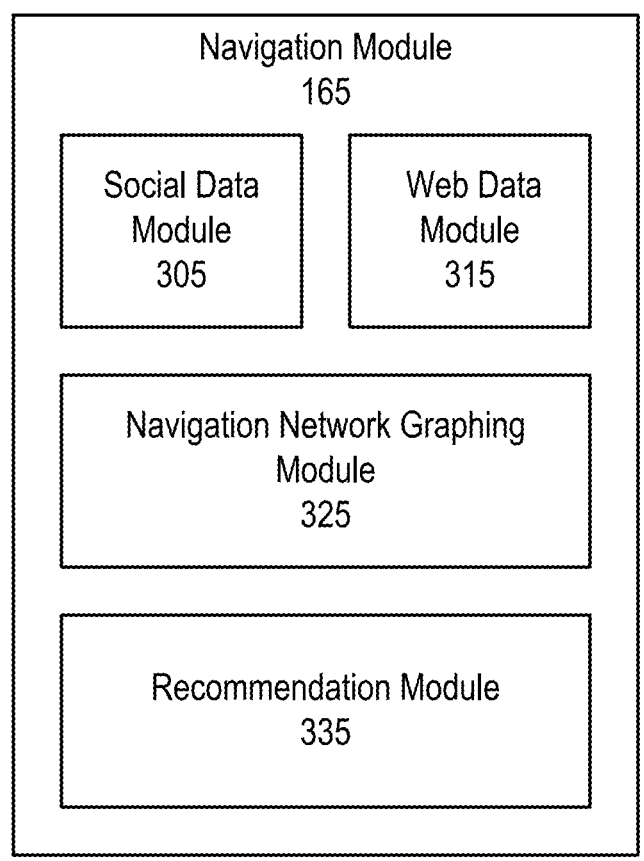
FIG. 3 is a block diagram illustrating a detailed view of the navigation module according to one embodiment.

FIG. 3 is a block diagram illustrating the navigation module 165 of the navigation server 155 according to one embodiment. The navigation module 165 includes a social data module 305, a web data module 315, a navigation network graphing module 325 hereon "graphing module", and a recommendation module 335.

The social data module 305 determines a social networking entity's relationship with other entities in the navigation network and transmits information about the entity's determined relationships to the graphing module 325. The determined information is used by the recommendation module 335 to recommend online content to the user.

In one embodiment, the social data module 305 determines the information about the entity's relationships by querying an external service to receive the relationship information from the external service. In another embodiment, the social data module 305 retrieves social graphs stored on the social network server 135, determines a social networking entity's relationship with other entities in the navigation network, and transmits the information to the graphing module 325. Additionally, embodiments of the social data module 305 associate strengths with the determined relationships of the entity based on the social relevance of the other entities to the entity. Social relevance accounts for the type or number of interactions an entity has with another entity or interest the entity exhibits in another entity. The determined relationships and relationship strengths are used by the recommendation module 335 to determine recommendations and associated information that are socially relevant to the browser account.

In one embodiment, the social data module 335 determines the social relevance between two entities based on the type of one entity's interaction with the other. For example, explicit interactions such as "likes" or "friends" are stronger than a visit to an entity's profile or a webpage. Additionally, the social data module 305 modifies the strength of the relationship based on the number of interactions. For example, if user X visits webpage A more often over a specified timeframe than webpage B, the social data module 305 determines the social relevance of webpage A to user X is stronger than that of webpage B.

In one embodiment, the social data module 305 determines the social relevance between two entities based on one entity's interest in the other entity's activities. For example, if entity X frequently posts recent news articles and entity Y oftentimes views the posted articles or if entity Y posts messages to entity X's profile, the social data module 305 determines that entity X is socially relevant to entity Y. Additionally, the social data module 305 can determine the strength of X's and Y's relationship based on the ratio of material posted by entity X to X's material viewed by entity Y.

In one embodiment, the social data module 305 processes social graphs to determine relationships between two entities based on content relevance. Two entities are content relevant if their profiles or web pages have a similar or shared keyword or category. For example, the profiles of known country artists are content relevant to country music, even if the profiles themselves did not interact. Further, in one embodiment, the social data module 305 determines a strength to associate with a relationship between two entities based on the degree of their content relevance. For example, if entities X and Y share characteristics such as a category and several keywords and entities X and Z share fewer keywords, X and Y have a higher degree of content relevance and thus have a stronger relationship.

The web data module 315 retrieves information about a user's browsing activities from the user's browser 115 and processes the received information to determine the user's areas of interest. The determined areas of interest are used by the recommendation module 335 to recommend online content to the user.

The web data module 315 determines the user's areas of interests based on an analysis of the web content accessed by the user as indicated in the user's browsing activities. For example, the web data module 315 analyzes and determines metadata, like keywords, associated with the accessed content. Additional examples of metadata include categories describing the web content, the type of web content, URLs associated with the web content, a rank or other statistic, related websites or search terms associated with the web content. The web data module 315 transmits this metadata to the graphing module 325 and the graphing module 325 stores these keywords as the user's area of interest.

Additionally, in one embodiment, the web data module 315 determines a user's interest strength associated with the user's areas of interest. The interest strength is used to rank the user's areas of interest in determining recommendations for the user. In one embodiment, the web data module 315 determines the interest strength between the user and an area of interest based on the frequency with which the user accesses content with metadata related to the area of interest. For example, the user's interest strength for "football" may be stronger than "basketball" because the user visits web sites associated with football teams more than the web sites associated with basketball teams.

In one embodiment, the web data module 315 may assign different weights to various metadata for determining the interest strength based on the hierarchy of the categories within the metadata. For example, keyword "football" and "basketball" may both belong to the "sports" category. Accordingly, the web data module 315 may determine both football and sports as areas of interest for a user visiting a web site associated with football. However, because "football" is a more specific keyword or later down the hierarchy of keywords than "sports", the web data module 315 associates a higher relationship strength for user's interest in football than user's interest in sports.

The graphing module 325 stores information about an entity's or a user's relationships with other entities and about the user's areas of interest received from the social data module 305 and the web data module 315. The graphing module 325 stores the received information as navigation network information for a user in the navigation database 175. Embodiments of the graphing module 325 repeatedly update the user's navigation network at specified intervals or in response to receiving data. In one embodiment, the received information about a user's content relevance with other entities includes an identifier such as a URL for entities that are content relevant to user's website, associated content relevance strengths, and metadata describing the content relevant entities. The received information about the user's areas of interest includes the keywords associated with the user's area of interest and interest strengths corresponding to the keywords. The received information about the user's relationships includes an identity such as an account identifier or profile URL of the entities that are socially relevant to the user, associated strength information, and associated metadata.

The recommendation module 335 receives navigation requests from the user's browser 115, determines corresponding navigation recommendations based on the requesting user's navigation network, and transmits the determined navigation recommendations to the browser 115. In one embodiment, a navigation request from a browser 115 includes request information such as a keyword, category, content identifier, or user's identity which the recommendation module 335 uses to determine a corresponding navigation recommendation. In one embodiment, the recommendation module 335 determines entities (e.g., websites) that are content relevant to the request based on the request's information and the entities' information. For example, the recommendation module 335 analyzes the entities' metadata and determines whether the metadata matches the keywords, categories, identity or URLs associated with the request.

In some embodiments, the recommendation module 335 receives navigation request from the user's browser 115 associated with updating a feed. The browser 115 may continually request updates for the feed and the recommendation module 335 handles the request as described above. In other instances, the recommendation module 335 may store the request in the navigation network and push navigation recommendations for updating the feed to the browser 115 as the graphing module 325 stores additional information in association with the request (e.g., changing the mapping of the request) in real time.

Additionally, in one embodiment, the recommendation module 335 may further map the request to a particular section of a website based on the content and metadata associated with that section. For example, the recommendation module 335 maps the football section of a sports news website with a request for "football news." If a feed is being generated based on the request, the recommendation module 335 may map the request to the football sections of various sports news websites. In another example, the recommendation module 335 may map the request to only a particular website or section of the website if a feed specific to the website or section of the website is being requested.

Once the recommendation module 335 maps the request and determines one or more content relevant entities, in one embodiment, the recommendation module 335 determines which content relevant entities are socially relevant to the user or related to interests of the user. The recommendation module 335 includes a set of these socially relevant and content relevant entities as browsing recommendations in the navigation recommendation. In one embodiment, the recommendation module 335 determines whether to include a content relevant entity in the recommendation set by crosschecking the relationships of the content relevant entity against the requesting user's relationships. The crosschecking indicates which entities, or "shared connections," in the user's navigation network, such as social networking friend, are related to both the crosschecked entity and the user's browser account. The recommendation module 335 analyzes the shared connections' relationship to the crosschecked entity and the shared connections' relationship to the user's browser account to determine whether or not to include the crosschecked entity as a browsing recommendation in the navigation recommendation. Referring to the above mentioned example, the recommendation module 335 may determine that the requesting user's friends have either viewed, recommended or posted the sports news website to a social networking profile, and therefore the recommendation module 335 may include the sports news website in the recommendation set for the requesting user.

In one embodiment, the recommendation module 335 analyzes the strengths associated with the relationships between the requesting user, the crosschecked entity and the shared connections to determine a social relevance score for the crosschecked entity. The strengths may be associated with relationships between the entity and the shared connections or between the shared connections and the requesting user. For example, if a shared connection is a social networking entity, the social relevance score takes into account the social relevance strength associated with the relationship between the shared connection and the user's browsing account and the strength associated with the relationship between the shared connection and the crosschecked entity. The strength associated with the relationship between the shared connection and the crosschecked entity may be based on social relevance, a determined interest of the shared connection or content relevance. The recommendation module 335 ranks entities based on their social relevance scores and selects top ranked results as browsing recommendations.

Additionally, in some embodiments, the recommendation module 335 also ranks the entities that are content relevant to the request based on the requesting user's area of interests. The recommendation module 335 analyzes the areas of interest for the requesting user and the entity to determine an interest score for the entity. For example, if the requesting user and the content relevant entity both have a similar area of interest, the interest score is based on the requesting user's and entity's interest strength for that area of interest. The interest score is based on the interest strength associated with the relationship between the determined similar interest and the browser account and the strength associated with the relationship between the determined similar interest and the entity. After determining the interest scores for various content relevant entities, the recommendation module 335 ranks the entities based on their interest scores and selects top ranked results as browsing recommendations.

In one embodiment, after ranking the content relevant entities based on their social relevance to the requesting user and their areas of interest that are similar to the requesting user, the recommendation module 335 includes the ranked entities in their ranked order in the recommendation set. The recommendation module 335 ranks the social relevant entities above the entities with similar areas of interest or vice versa.

In some embodiments, the recommendation module 335 includes connection information as associated information for the browsing recommendations in the navigation recommendation. The connection information indicates, to the requesting user, the user's relationship to a browsing recommendation. For recommended entities with similar areas of interest as the requesting user, the recommendation module selects the keywords indicating the similar areas of interest as the connection information.

For socially relevant entities, the recommendation module 335 includes in connection information the information about the shared connection between the requesting user and the recommendation. Examples of such connection information include descriptions or images of the shared connection, the shared connection's interaction with the browsing recommendation, a content identifier or social networking identity associated with the shared connection or other metadata stored in the navigation network. For example, if the shared connection "liked" the browsing recommendation, the recommendation module 335 includes metadata indicating that the shared connection "liked" the recommendation. Additionally, the included metadata can be a profile name and URL (or image) of a profile picture or logo of the shared connection. For example, if the shared connection is an online entity or a category thereof, the included metadata can be a description of associated web content, keyword or URL (or image) of the web content or category. In one embodiment, the metadata includes the total number of users or the number of the user's friends who liked or viewed the recommendation.

Additionally, in some embodiments, the recommendation module 335 retrieves from the requesting user's navigation network, relationship strengths between the user and the shared connections. The recommendation module 335 then ranks the shared connections based on the retrieved relationship strengths and selects one or more top ranked shared connections. The recommendation module 335 includes information about the selected shared connections as associated information for the browsing recommendation.

Example Computing Device

Figure 4:
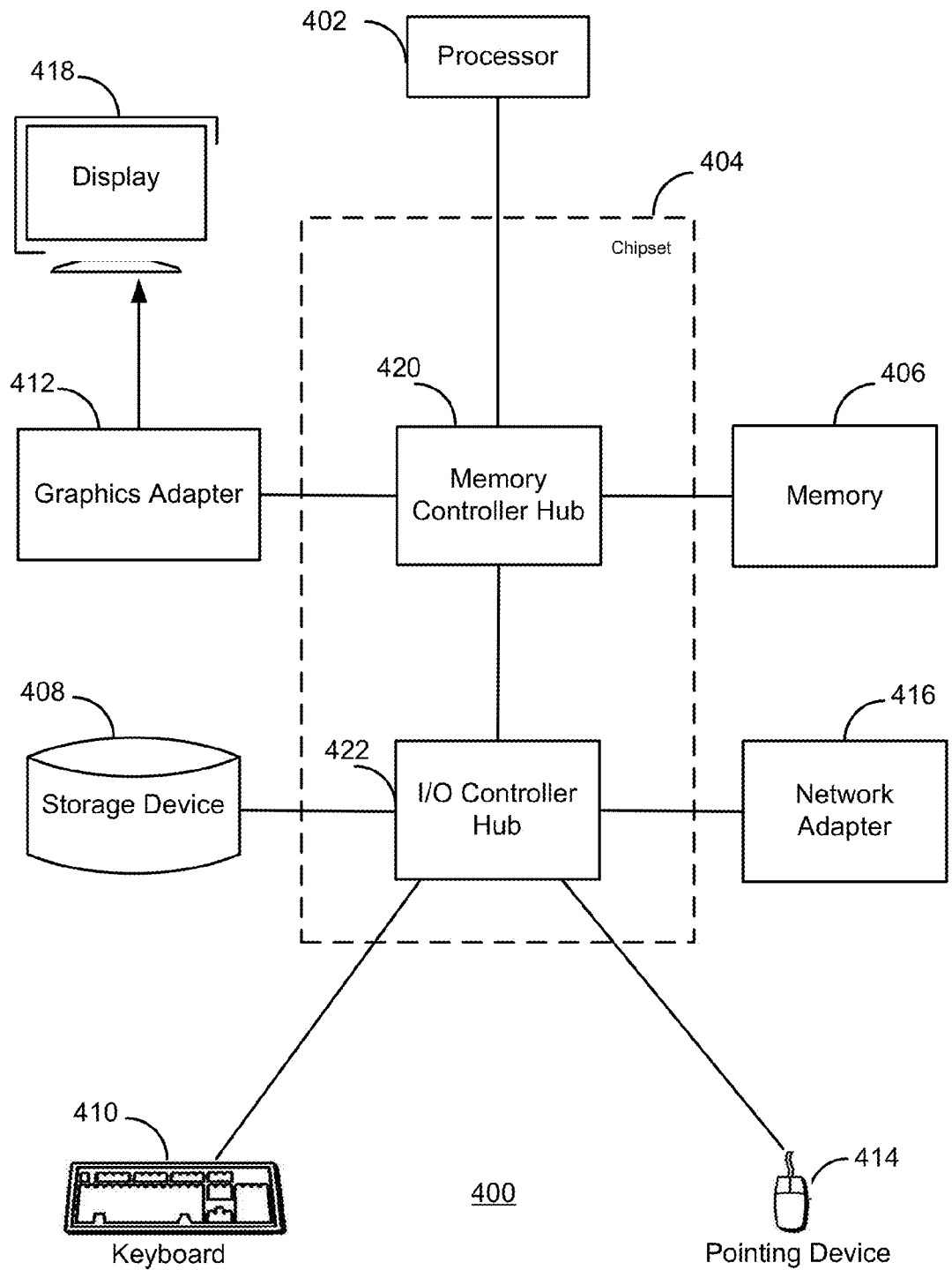
FIG. 4 is a block diagram illustrating an example of a computer for use as a client or server according to one embodiment.

FIG. 4 is a high-level block diagram illustrating an example of a computer 400 for use as a client 105 or server 155 according to one embodiment. Illustrated are at least one processor 402 (CPU) coupled to a chipset 404. The chipset 404 includes a memory controller hub 420 and an input/output (I/O) controller hub 422. A memory 406 and a graphics adapter 413 are coupled to the memory controller hub 420, and a display device 418 is coupled to the graphics adapter 413. A storage device 408, keyboard 410, pointing device 414, and network adapter 416 are coupled to the I/O controller hub 422. Other embodiments of the computer 400 have different architectures. For example, the memory 406 is directly coupled to the processor 402 in some embodiments.

The storage device 408 is a non-transitory computer-readable storage medium such as a hard drive, compact disk read-only memory (CD-ROM), DVD, or a solid-state memory device. The memory 406 holds instructions and data used by the processor 402. The pointing device 414 is used in combination with the keyboard 410 to input data into the computer system 400. The graphics adapter 412 displays images and other information on the display device 418. In some embodiments, the display device 418 includes a touch screen capability for receiving user input and selections. The network adapter 416 couples the computer system 400 to the network 125. Some embodiments of the computer 400 have different or other components than those shown in FIG. 4. For example, the server 155 may be formed of multiple blade servers and lack a display device, keyboard, and other components.

As used herein, the term "module" refers to computer program instructions or other logic used to provide the specified functionality. Thus, a module can be implemented in hardware, firmware, or software. In one embodiment, program modules formed of executable computer program instructions are stored on the storage device 408, loaded into the memory 406, and executed by the processor 402 as one or more processes.

Navigation Recommendation Methodology

Figure 5:
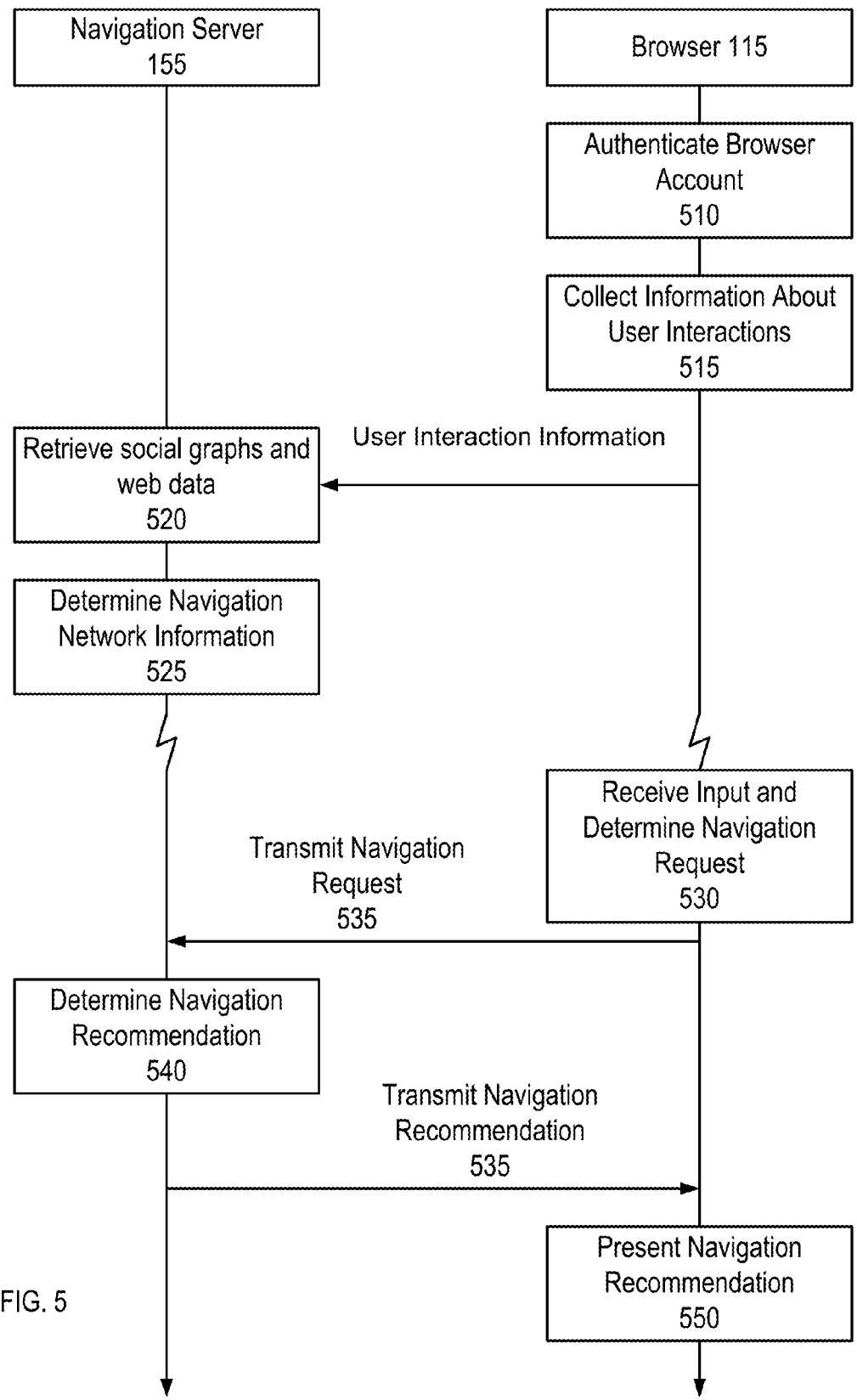
FIG. 5 is a trace diagram illustrating a method of guiding web navigation according to one embodiment.

FIG. 5 is a trace diagram illustrating a method of guiding web navigation according to one embodiment. The browser 115 authenticates the browser account of a user and associates the user's social networking accounts and web data services with the browser account.

The browser 115 collects information about the user's interactions with information displayed at the browser 115. Collected information, such as the user's browsing activities, includes frequency values of searches or accesses of web content and time values describing the amount of time the user spent viewing the web content. The browser 115 transmits the information about the user's interactions to the navigation server 155.

The navigation server 155 retrieves 520 social graph and web data information corresponding to various user's social network accounts and web data services from social networking servers 135 and web data servers 145. The navigation server 155 also retrieves 520 web data information including descriptions, rankings and keywords or categories of online entities and associated web content from the web data servers 145. The browser 115 and navigation server 155 can perform steps 515 and 520 repeatedly as the browser 115 stores, requests or determines new data.

The navigation server 155 determines 525 relationships and relationship strengths for social networking entities and online entities identified in the retrieved information. Additionally, the navigation server 155 determines 525 relationships and relationship strengths for the user's browser account based on user specific data such as the user's browsing activity and associated social graphs.

The browser 115 receives input requesting a navigation recommendation and determines 530 a navigation request. When the browser 115 receives textual input, the request includes the entered text, indicates where the input was received and identifies the browser account. In other embodiments, the request includes different information such as a URL, keyword, category or social networking identity associated with the input. The browser 115 transmits the navigation request 535 to the navigation server.

The navigation server 155 receives the transmitted 535 navigation request and determines 540 a navigation recommendation including one or more browsing recommendations and associated information for the browsing recommendations. The navigation server 155 transmits 535 the navigation recommendation to the browser 115. The browser presents 550 the navigation recommendation to the user. Several embodiments illustrating the presentation of navigation recommendations are discussed below with reference to FIGS. 6, 7 and 8 below.

Other embodiments can perform the steps of the method in different orders and can include different or additional steps. In addition, some or all of the steps can be performed by entities other than the navigation server 155 and browser 115.

Example Navigation Recommendations

Figure 6:
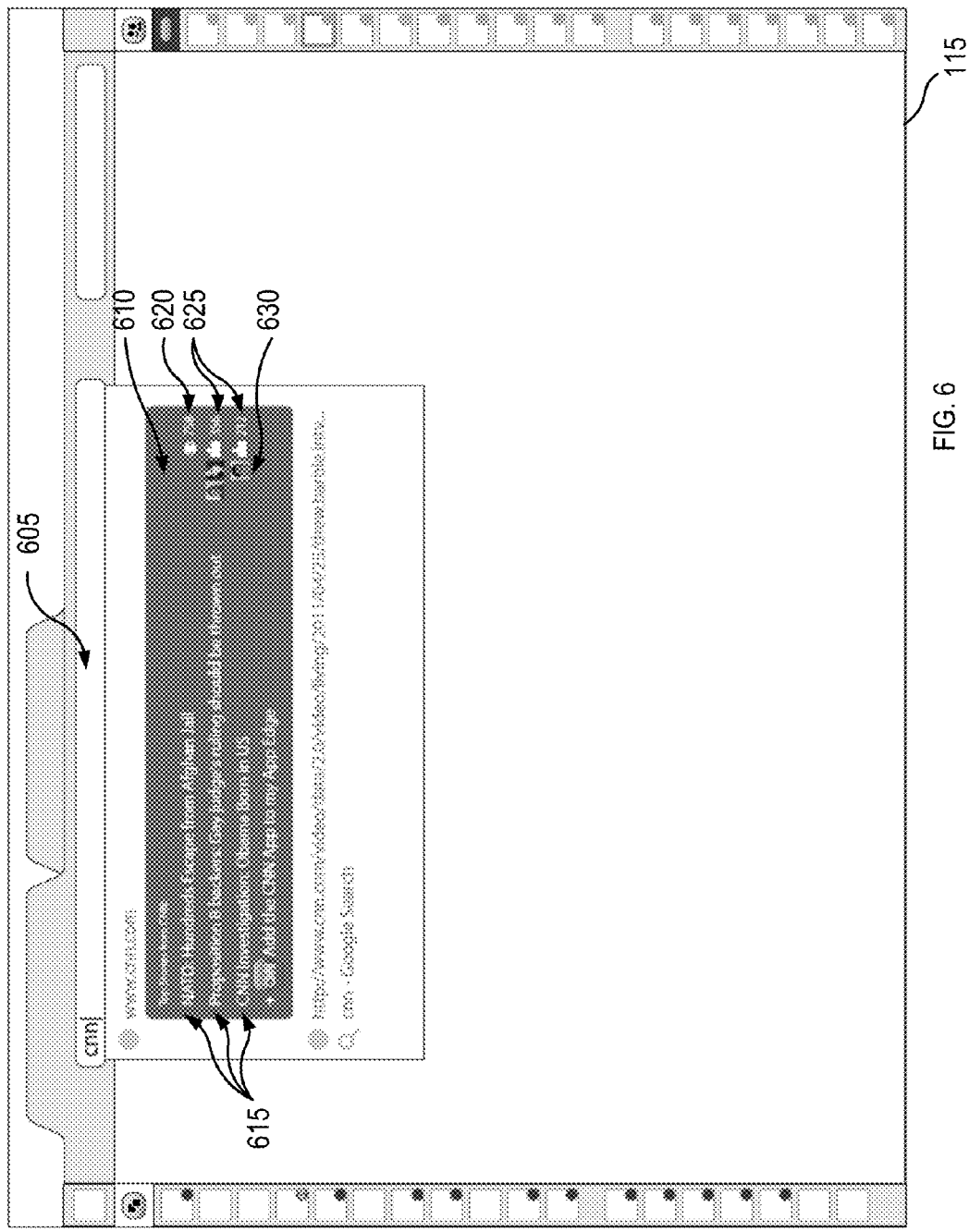
FIG. 6 is a user interface illustrating an input received at an address bar of a browser and corresponding navigation recommendation presented by the browser according to one embodiment.

FIG. 6 is a user interface illustrating an input received at an address bar 605 of a browser 115 and a corresponding navigation recommendation 610 presented by the browser 115 according to one embodiment. As shown in FIG. 6, the browser 115 receives textual user input "cnn" at address bar 605 and prepares a request that includes the entered text and indicates that the input was received at the address bar 605. Additionally, the request can indicate a number of browsing recommendations 615 to receive. The browser 115 transmits the request to the navigation server 155. The navigation server 155 determines a navigation recommendation 610 including one or more browsing recommendations 615 and associated information 620, 625, 630 based on the received request and transmits the determined navigation recommendation to the browser 115. When the browser 115 receives the corresponding navigation recommendation 610, it presents the browsing recommendations 615 and their associated information, such as views 620, likes ("thumbs-ups", shares, etc.) 625, and shared connections 630 proximate to the address bar 605. The user can select a browsing recommendation 615 to navigate to it and select or view the associated information. Additionally, the user can request a new navigation recommendation or additional browsing recommendations by inputting new or additional text at the address bar 605. In the illustrated embodiment, the navigation recommendation 610 includes images of shared connections 630 that interacted with the browsing recommendations 615 (or content threat) and are social networking friends of the requesting user. In one embodiment, each shared connection 630 "liked" the browsing recommendation 615 he/she is associated with and images of one or more of the shared connections are displayed proximate to the total number of likes 625 received for the browsing recommendation. The browser 115 presents the shared connections 625 and number of likes 625 adjacent to the respective browsing recommendation 615. Thus, the user can choose which browsing recommendation 615 to access based not only on the description, but which, and how many shared connections liked the browsing recommendation.

Figure 7:
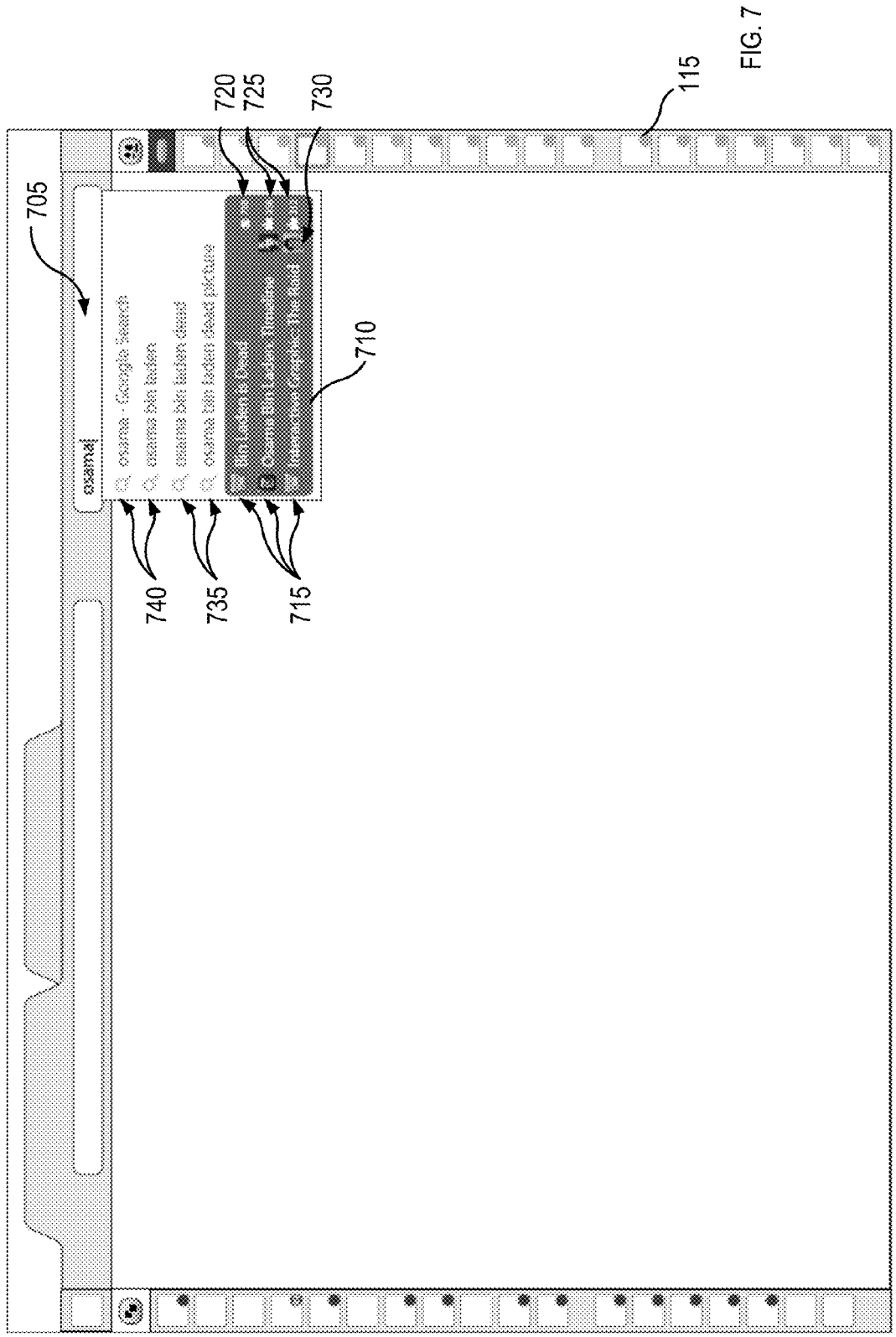
FIG. 7 is a user interface illustrating an input received at a search bar of a browser and corresponding navigation recommendation presented by the browser according to one embodiment.

FIG. 7 is a user interface illustrating an input received at a search bar 705 of a browser 115 and a corresponding navigation recommendation 710 presented by the browser 115 according to one embodiment. As shown in FIG. 7, the browser 115 receives textual user input "osama" at search bar 705 and prepares a request that includes the entered text and indicates that the input was received at the search bar 705. The browser 115 transmits the request to the navigation server 155 and receives a corresponding navigation recommendation 710 that includes browsing recommendations 715 and associated information 720, 725, and 730 which are displayed to the user.

In some embodiments, the browser 115 receives search suggestions with the navigation recommendation 710. The browser 115 can present the search suggestions 735 with the browsing recommendations 715 in the navigation recommendation 710 or at another location proximate to the search bar 705. The illustrated embodiment shows an example of search suggestions 735 presented with the browsing recommendations 715. The browser 115 can request additional browsing recommendations or associated information 720, 725, 730 to receive for search suggestions 735 or other data presented in the search bar 705. For example, if the user scrolls over a search suggestion 735, additional browsing recommendations are requested and presented. The additional browsing recommendations and associated content may be displayed in a window or menu generated by the browser 115 adjacent to the selection. Alternatively, recommendations and associated content may be presented underneath the selected search suggestion or replace the currently displayed browsing recommendations 715. In other embodiments, the browser may receive search suggestions 740 from another service, transmit the search suggestions to the navigation server 155, receive corresponding navigation recommendations and display the received navigation recommendation.

Figure 8:
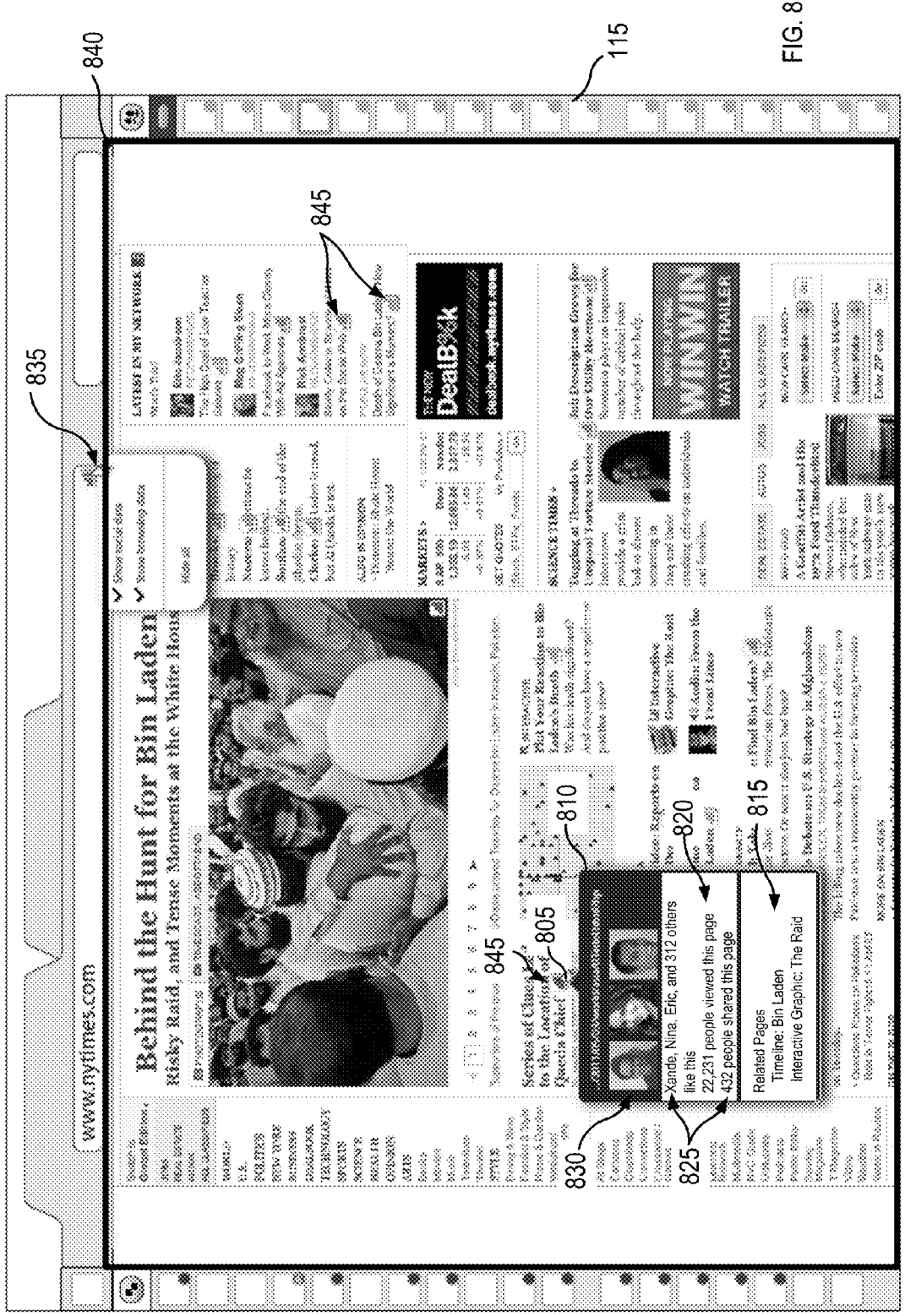
FIG. 8 is a user interface illustrating an input received as a selection within a browser and corresponding navigation recommendation presented by the browser according to one embodiment.

FIG. 8 is a user interface illustrating an input received as a selection 805 within a browser 115 and a corresponding navigation recommendation 810 presented by a browser 115 according to one embodiment. As shown in FIG. 8, the browser 115 receives, as user input, a selection 805 within web content 840 displayed by the browser. Consequently, the browser 115 prepares a request that includes a URL of the selected content or data describing the selected content such as metadata or an identifier and indicates that input was received as selection 805.

In one embodiment, the browser 115 detects the selection 805 of a selectable navigation element 845 and requests a corresponding navigation recommendation. In one embodiment, the received navigation recommendation 810 includes associated information 820, 825, 830 for a URL corresponding to the selected navigation element and additional browsing recommendations 815 and optionally associated information for the additional recommendations. In one embodiment, the associated information for the browsing recommendations 815 is received and displayed responsive to the user scrolling over a recommendation. Various combinations of the above or other techniques discussed herein may be implemented to display navigation recommendations, search suggestions, browsing recommendations and associated information in other ways within the browser 115.

Figure 9:
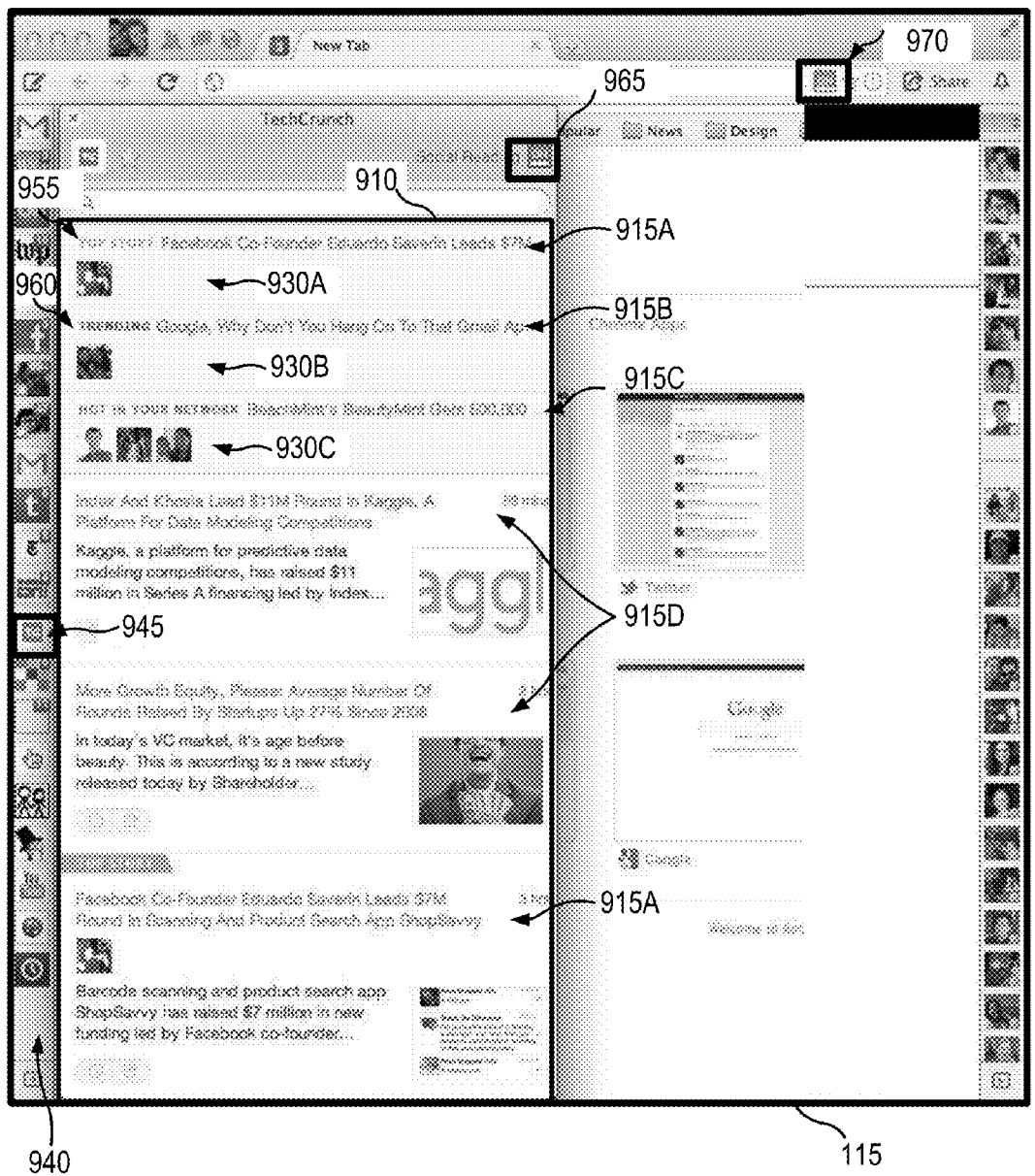
FIG. 9 is a user interface illustrating a navigation recommendation 910 presented by a browser 115 for updating a feed according to one embodiment.

FIG. 9 is a user interface illustrating a navigation recommendation 910 presented by a browser 115 for updating a feed according to one embodiment. As shown in FIG. 9, the browser 115 receives a selection 945 of an icon within a feed pane 940 displayed by the browser. The feed pane 940 displays icons associated with URLs or keywords for which the browser 115 receives navigation recommendations as feed updates from the navigation server 155. The user selects 945 an icon in the feed pane 940 to view a corresponding navigation recommendation 910 for the selected feed. One example navigation recommendation 910 for selected feed 945 includes browsing recommendations 915 and optionally associated information such as images of shared connections 930 having interacted with a recommendation or rankings of the browsing recommendations. For example, images of shared connections 930A-C are displayed with browsing recommendation 915A-C. In some embodiments, the browser 115 displays the browsing recommendations 915 within the navigation recommendation 910 according to their rankings in the user's navigation network. For example, navigation recommendation 910 displays the highest ranked browsing recommendation 915A as the "top story" 955 with additional information below and browsing recommendation 915B increasing in rank as "trending" 960. Other high ranked browsing recommendations such as 915C and additional recommendations 915D may be displayed below.

FIG. 9 also illustrates an on-off option 965 associated with the selected 945 feed for the user to specify whether they want to opt in or out of sharing their browsing activity with other users while browsing website domains associated with the feed. Additionally, a social browsing notification icon 970 is displayed to the user if the browsing activity on a currently displayed webpage is being collected and shared with other users. Selecting the notification icon 970 may display (not shown) the feeds associated with the currently viewed webpage and provide the user with options to opt in or out of sharing their browsing activity with a particular feed or while browsing the viewed webpage or domain.

The foregoing description of the embodiments of the invention has been presented for the purpose of illustration; it is not intended to be exhaustive or to limit the invention to the precise forms disclosed. Persons skilled in the relevant art can appreciate that many modifications and variations are possible in light of the above disclosure.

Some portions of this description describe the embodiments of the invention in terms of algorithms and symbolic representations of operations on information. These algorithmic descriptions and representations are commonly used by those skilled in the user interface arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Any of the steps, operations, or processes described herein may be performed or implemented with one or more hardware or software modules, alone or in combination with other devices. In one embodiment, a software module is implemented with a computer program product comprising a non-transitory computer-readable storage medium containing computer program code, which can be executed by a computer processor for performing any or all of the steps, operations, or processes described. Further, unless expressly states to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Embodiments of the invention may also relate to an apparatus for performing the operations herein. This apparatus may be specially constructed for the required purposes, or it may comprise a general-purpose computing device selectively activated or reconfigured by a computer program stored in the computer. Such a computer program may be stored in a non transitory, tangible computer readable storage medium, or any type of media suitable for storing electronic instructions, which may be coupled to a computer system bus. Furthermore, any computing systems referred to in the specification may include a single processor or may be architectures employing multiple processor designs for increased computing capability.

Embodiments of the invention may also relate to a product that is produced by a computing process described herein. Such a product may comprise information resulting from a computing process, where the information is stored on a non transitory, tangible computer readable storage medium and may include any embodiment of a computer program product or other data combination described herein.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention, which is set forth in the following claims.

What is claimed is:

1. A computer-implemented method for guiding web navigation of a client at a server, the method comprising:

storing information about interactions of a plurality of users with content items on a network, each of the interactions including a corresponding one of the plurality of users posting about, accessing, tagging, liking, viewing, visiting, or sharing a corresponding one of the content items;

determining, for a viewing user of the plurality of users, one or more other users associated with the viewing user, the plurality of users including the one or more other users associated with the viewing user, wherein the one or more other users are social networking friends of the viewing user;

storing, for the viewing user, an indication of an association between the viewing user and the one or more other users;

receiving a request from a browser associated with the viewing user, the request including text and indicating that the text was received at a bar of the browser, wherein the bar is a search bar or an address bar;

determining a set of candidate content items related to the request;

determining a navigation recommendation for the viewing user based on the stored indication of the viewing user's association with the one or more other users and the interactions of the one or more other users with the set of candidate content items, the navigation recommendation pertaining to one or more content items selected from the set of candidate content items; and prior to submission of a search query or address via the bar, transmitting the navigation recommendation to the browser for display in a panel proximate to the bar as an extension of the bar, wherein the navigation recommendation includes a URL for a selected content item of the one or more content items selected from the set of candidate content items, a first indication of a type of interaction between a subset of the one or more other users related to the viewing user and the selected content item, a second indication of a number of the subset of the one or more other users that interacted with the content item, and an image of at least one of the subset of the one or more other users having interacted with the selected content item, wherein the image is from a social network the viewing user participates in, wherein the image, the first indication and the second indication are displayed in the panel proximate to the URL;

wherein the type of interaction between the subset of the one or more other users related to the viewing user and the selected content item includes posting about, accessing, tagging, liking, viewing, visiting, or sharing the URL.

2. The method of claim 1, wherein the navigation recommendation further comprises a description or title of the selected content item.

3. The method of claim 1, wherein the URL represents a website, webpage, or media.

4. The method of claim 1, wherein the information stored for a given user and a given selection of content items the given user interacted with comprises at least one of a duration, a type, or a frequency.

5. The method of claim 1, wherein a strength of the association between the viewing user and the set of candidate content items is based on at least one of a type, a duration, or a frequency of each interaction.

6. The method of claim 1, wherein determining the one or more other users associated with the viewing user comprises an analysis of a social graph retrieved from a social network participated in by the viewing user.

7. The method of claim 1, wherein determining a navigation recommendation comprises:
   determining a content relevance of content items to the request, the content relevance describing the degree to which a content item is contextually relevant to the request, and selecting the set of candidate content items based on a ranking of content relevance; and
   crosschecking a candidate content item against the associations of the viewing user with the one or more other users to determine which of the one or more other users interacted with the candidate content item.

8. The method of claim 7, wherein determining the navigation recommendation comprises selecting the candidate content item for the navigation recommendation based on at least one of an identity of the one or more other users that interacted with the candidate content item, how many of the one or more other users that interacted with the candidate content item, or a type of association between the viewing user and each of the one or more other users that interacted with the candidate content item.

9. The method of claim 1, wherein determining the navigation recommendation comprises determining associated information for the selected content items, the associated information including one or more of:
   identities of a subset of the one or more other users associated with the viewing user that interacted with the selected content item, wherein the subset of the one or more other users is determined based on:
      a type of interaction with the selected content item;
      a frequency of interaction with the selected content item; or
      a duration of interaction with the selected content item.

10. The method of claim 1, wherein determining a navigation recommendation for the viewing user is performed based, at least in part, on a social relevance strength associated with relationships between the viewing user and the one or more other users.

11. The method of claim 1, further comprising:
   presenting an opt-in option, enabling the viewing user to opt in or out of sharing browsing activity with others.

12. The method of claim 11, further comprising:
   receiving, from the viewing user, an indication that the viewing user is opting in to share their browsing activity with others; and
   transmitting to the browser for display to the viewing user, a browsing notification that the browsing activity of the user is being shared with others.

13. The method of claim 11, wherein the opt-in option is presented in association with a particular feed, web page, or domain.

14. The method of claim 1, wherein the network is a social network.

15. The method of claim 1, wherein the bar is an address bar.

16. The method of claim 1, wherein the navigation recommendation includes
   one or more search terms.

17. The method of claim 1, the method further comprising:
   receiving the information from one or more social network servers.

18. The method of claim 1, wherein the information comprises a social graph describing, for each of the interactions, a type of the interaction.

19. A computer-implemented method of guiding web navigation at a browser, the method comprising:
   associating a viewing user in a navigation network with the browser, the navigation network storing information about associations between the viewing user and a plurality of users, and interactions of the plurality of users with content items on the navigation network, the plurality of users being social networking friends of the viewing user;
   receiving, at a bar of the browser, text including a keyword, wherein the bar is a search bar or an address bar;
   preparing, by the browser, a request that includes the text and indicates that the text was received at the bar of the browser;
   transmitting the request prior to submission of a search query or address via the bar;
   receiving a navigation recommendation based on the request and the information stored in the navigation network, the navigation recommendation including a URL for a content item, a first indication of a type of interaction between a subset of the plurality of users and the content item, a second indication of a number of the subset of the plurality of users that interacted with the content item, and an image of at least one of the subset of the plurality of users having interacted with the selected content item, wherein the image is from a social network the viewing user participates in; and
   presenting the navigation recommendation in a panel proximate to the bar as an extension of the bar, the presentation including a display of the URL for the content item proximate to the first indication of the type of interaction between the subset of the plurality of users and the content item, proximate to the second indication of the number of the subset of the plurality of users that interacted with the content item, and proximate to the image;
   wherein the type of interaction between the subset of the plurality of users associated with the viewing user and the selected content item includes posting about, accessing, tagging, liking, viewing, visiting, or sharing the URL.

20. The method of claim 19, wherein the URL represents a website, webpage, or media.

21. The method of claim 19, wherein the navigation recommendation further comprises a description or title of the content item.

22. The method of claim 19, wherein the URL represents a website, webpage, or media the subset of the plurality of users interacted with.

23. The method of claim 19, the method further comprising an analysis of web content retrieved for a webpage, the analysis including:
   determining content items in received web content for association with navigation icons;

transmitting information about a given content item in the request in response to the viewing user of the browser selecting the associated navigation icon; and displaying the navigation recommendation proximate to the selected navigation icon.

24. The method of claim 19, wherein the bar is an address bar.

25. An apparatus, comprising:

a processor; and a memory, at least one of the processor or the memory being configured to:

store information about interactions of a plurality of users with content items on a network, each of the interactions including a corresponding one of the plurality of users posting about, accessing, tagging, liking, visiting, or sharing a corresponding one of the content items;

determine, for a viewing user of the plurality of users, one or more other users associated with the viewing user, the plurality of users including the one or more other users associated with the viewing user, the one or more other users being social networking friends of the viewing user;

store, for the viewing user, an indication of an association between the viewing user and the one or more other users;

receive a request from a browser associated with the viewing user, the request including text and indicating that the text was received at a bar of the browser, wherein the bar is a search bar or an address bar;

determine a set of candidate content items related to the request;

determine a navigation recommendation for the viewing user based on the stored indication of the viewing user's association with the one or more other users and the interactions of the one or more other users with the set of candidate content items, the navigation recommendation pertaining to a content item selected from the set of candidate content items; and prior to submission of a search query or address via the bar, transmit the navigation recommendation to the browser for display in a panel proximate to the bar as an extension of the bar, wherein the navigation recommendation includes a URL for the selected content item, a first indication of a type of interaction between a subset of the one or more other users related to the viewing user and the selected content item, a second indication of a number of the subset of the one or more other users that interacted with the content item, and an image of at least one of the subset of the one or more other users having interacted with the selected content item, wherein the image is from a social network the viewing user participates in, where the image, the first indication and the second indication are displayed in the panel proximate to the URL;

wherein the type of interaction between the subset of the one or more other users related to the viewing user and the selected content item includes posting about, accessing, tagging, liking, sharing, viewing, or visiting the URL.

26. The apparatus of claim 25, wherein the bar is an address bar.

* * * * *